(12) United States Patent
Hodges et al.

(10) Patent No.: US 6,284,125 B1
(45) Date of Patent: *Sep. 4, 2001

(54) ELECTROCHEMICAL CELL

(75) Inventors: Alastair McIndoe Hodges, San Diego; Thomas William Beck, New South Wales; Oddvar Johansen, Mulgrawe, all of (AU)

(73) Assignee: USF Filtration and Separations Group, Inc., Timonium, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 27 days.

This patent is subject to a terminal disclaimer.

(21) Appl. No.: 08/981,385
(22) PCT Filed: Jun. 19, 1996
(86) PCT No.: PCT/AU96/00365
  § 371 Date: Apr. 17, 1998
  § 102(e) Date: Apr. 17, 1998
(87) PCT Pub. No.: WO97/00441
  PCT Pub. Date: Jan. 3, 1997

(30) Foreign Application Priority Data

Jun. 19, 1995 (AU) .................................................. PN 3639

(51) Int. Cl.[7] .................................................. G01N 27/26
(52) U.S. Cl. ........................ 205/775; 205/775.5; 205/778; 205/780.5; 205/782.5; 205/792; 204/403; 204/412; 204/415
(58) Field of Search .................................. 204/403, 412, 204/415; 205/775, 775.5, 778, 780.5, 782.5, 792

(56) References Cited

U.S. PATENT DOCUMENTS 4,224,125  9/1980  Nakamura et al. .............. 204/195 B (List continued on next page.)

FOREIGN PATENT DOCUMENTS

A 54873/94  2/1993  (AU) .

(List continued on next page.)

OTHER PUBLICATIONS

"Electrochemical Behavior of Reversible Redox Species at (List continued on next page.)

*Primary Examiner*—Bruce F. Bell
(74) *Attorney, Agent, or Firm*—Knobbe, Martens, Olson, and Bear LLP

(57) ABSTRACT

A method for determining the concentration of a reduced (or oxidised) form of a redox species in an electrochemical cell of the kind comprising a working electrode and a counter electrode spaced from the working electrode by a predetermined distance, said method comprising the steps of: (1) applying an electric potential difference between the electrodes; (2) selecting the potential of the working electrode such that the rate of electro-oxidation of the reduced form (or electro-reduction of the oxidised form) of the species is diffusion controlled, (3) selecting the spacing between the working electrode and the counter electrode so that reaction products from the counter electrode arrive at the working electrode; (4) determining current as a function of time after application of the potential and prior to achievement of a steady state; (5) estimating the magnitude of the steady state current, and (6) obtaining from the change in current with time and the magnitude of the steady state current, a value indicative of the diffusion coefficient and/or of the concentration of the reduced form (or the oxidised form) of the species. Also disclosed is an apparatus for determining the concentration of a redox species in an electrochemical cell comprising: an electrochemical cell having a working electrode and a counter (or counter/reference) electrode, means for applying and electric potential difference between said electrodes, means for measuring the change in current with time, and characterised in that the working electrode is spaced from the counter electrode by less than 500 µm.

108 Claims, 5 Drawing Sheets

U.S. PATENT DOCUMENTS

| | | | |
|---|---|---|---|
| 4,233,029 | 11/1980 | Columbus | 23/230 R |
| 4,254,083 | 3/1981 | Columbus | 422/55 |
| 4,259,165 | 3/1981 | Miyake | 204/415 |
| 4,301,412 | 11/1981 | Hill et al. | 324/442 |
| 4,301,414 | 11/1981 | Hill et al. | 324/446 |
| 4,303,887 | 12/1981 | Hill et al. | 324/441 |
| 4,307,188 | 12/1981 | White | 435/4 |
| 4,374,013 | 2/1983 | Enfors | 204/195 |
| 4,404,066 | 9/1983 | Johnson | 204/1 |
| 4,431,004 | 2/1984 | Bessman et al. | 128/635 |
| 4,517,287 | 5/1985 | Scheibe et al. | 435/4 |
| 4,517,291 | 5/1985 | Seago | 435/14 |
| 4,533,440 | 8/1985 | Kim | 204/1 |
| 4,545,382 | 10/1985 | Higgins et al. | 128/635 |
| 4,552,840 | 11/1985 | Riffer | 205/778 |
| 4,629,563 | 12/1986 | Wrasidlo | 210/500.34 |
| 4,654,197 | 3/1987 | Lilja et al. | 422/56 |
| 4,664,119 | 5/1987 | Bessman et al. | 204/415 |
| 4,711,245 | 12/1987 | Higgins et al. | 128/635 |
| 4,774,039 | 9/1988 | Wrasidlo | 264/41 |
| 4,782,265 | 11/1988 | Schaper et al. | 313/483 |
| 4,790,925 | 12/1988 | Miller et al. | 204/415 |
| 4,900,424 | 2/1990 | Birth et al. | 204/409 |
| 4,919,770 | 4/1990 | Preidel et al. | 204/153.1 |
| 4,963,815 | 10/1990 | Hafeman | 205/777.5 |
| 5,059,908 | 10/1991 | Mina | 324/444 |
| 5,064,516 | 11/1991 | Rupich | 204/415 |
| 5,120,420 | 6/1992 | Nankai et al. | 204/403 |
| 5,122,244 | 6/1992 | Hoenes et al. | 204/153.1 |
| 5,126,034 | 6/1992 | Carter et al. | 204/403 |
| 5,128,015 | 7/1992 | Szuminsky et al. | 204/403 |
| 5,141,868 | 8/1992 | Shanks et al. | 435/288 |
| 5,151,166 | 9/1992 | Harral et al. | 204/425 |
| 5,192,415 | 3/1993 | Yoshioka et al. | 204/403 |
| 5,229,282 | 7/1993 | Yoshioka et al. | 435/177 |
| 5,243,526 | 9/1993 | White | 364/413.07 |
| 5,272,087 | 12/1993 | El Murr et al. | 435/291 |
| 5,320,732 | 6/1994 | Nankai et al. | 204/403 |
| 5,382,346 | 1/1995 | Uenoyama et al. | 204/403 |
| 5,384,028 | 1/1995 | Ito | 204/403 |
| 5,385,846 * | 1/1995 | Kuhn et al. | 204/403 |
| 5,393,399 | 2/1995 | Van den Berg et al. | 204/412 |
| 5,395,504 | 3/1995 | Saurer et al. | 204/403 |
| 5,413,690 | 5/1995 | Kost et al. | 204/403 |
| 5,437,999 | 8/1995 | Diebold et al. | 435/288 |
| 5,508,171 | 4/1996 | Walling et al. | 205/777.5 |
| 5,509,410 | 4/1996 | Hill et al. | 128/637 |
| 5,520,787 | 5/1996 | Hanagan et al. | 204/403 |
| 5,527,446 | 6/1996 | Kosek et al. | 204/403 |
| 5,567,302 | 10/1996 | Song et al. | 205/777.5 |
| 5,575,895 | 11/1996 | Ikeda et al. | 204/409 |
| 5,611,908 | 3/1997 | Mattiessen et al. | 205/775 |
| 5,620,579 | 4/1997 | Genshaw et al. | 204/402 |
| 5,628,890 | 5/1997 | Carter et al. | 204/403 |
| 5,645,709 | 7/1997 | Birch et al. | 205/775 |
| 5,682,884 | 11/1997 | Hill et al. | 128/637 |
| 5,726,565 | 3/1998 | Uchiyama et al. | 324/94 |
| 5,849,174 | 12/1998 | Sanghere et al. | 205/775 |
| 5,909,114 | 6/1999 | Uchiyama et al. | 324/94 |

FOREIGN PATENT DOCUMENTS

| | | |
|---|---|---|
| A-31042/93 | 7/1993 | (AU) . |
| WO 95/28634 * | 10/1995 | (AU) . |
| 3103 464 A1 | 8/1982 | (DE) . |
| 3103-464 | 8/1982 | (DE) . |
| 0 125 137 A2 | 11/1984 | (EP) . |
| 0 251 915 A2 | 1/1988 | (EP) . |
| 0 255 291 A1 | 2/1988 | (EP) . |
| 0 266 204 A2 | 4/1988 | (EP) . |
| 0 278 647 A2 | 8/1988 | (EP) . |
| 0 299 779 A2 | 1/1989 | (EP) . |
| 0 351 516 A2 | 1/1990 | (EP) . |
| 0 351 892 A2 | 1/1990 | (EP) . |
| 0 171 375 A1 | 5/1990 | (EP) . |
| 0 367 432 A1 | 5/1990 | (EP) . |
| 170375 | 5/1990 | (EP) . |
| 0 400 918 A1 | 12/1990 | (EP) . |
| 0 418 404 A1 | 3/1991 | (EP) . |
| 0 451 981 A2 | 10/1991 | (EP) . |
| 0 127 958 B2 | 3/1992 | (EP) . |
| 0 560 336 A1 | 9/1993 | (EP) . |
| 593096 A2 | 4/1994 | (EP) . |
| 0 609 760 A1 | 8/1994 | (EP) . |
| 0 735 303 A1 | 10/1996 | (EP) . |
| 0 406 304 B1 | 8/1997 | (EP) . |
| 2 020 424 A | 11/1979 | (GB) . |
| 2 154 735 A | 9/1985 | (GB) . |
| 2 201 248 A | 8/1988 | (GB) . |
| 2215846 | 9/1989 | (GB) . |
| 2 235 050 A | 2/1991 | (GB) . |
| 62 22874 | 10/1987 | (JP) . |
| 63139246 A2 | 6/1988 | (JP) . |
| 3 167464 | 7/1991 | (JP) . |
| 4 66112 A | 3/1992 | (JP) . |
| 1351-627 A | 11/1987 | (SU) . |
| WO 89/08713 | 9/1989 | (WO) . |
| WO 92/15701 | 9/1992 | (WO) . |
| WO 94/02842 | 2/1994 | (WO) . |
| WO-A-94/29731 | 12/1994 | (WO) . |
| WO 95/16198 | 6/1995 | (WO) . |
| WO-A-95/28634 | 10/1995 | (WO) . |
| WO 97/00441 | 1/1997 | (WO) . |

OTHER PUBLICATIONS

Interdigitated Array Electrodes with Different Geometries: Consideration of Redox Cycling and Collection"; Analytical Chemistry; Mar. 1990, vol. 62, No. 5, pp. 447–452).

Data Sheet for ARcare 7148 double–side adhesive coated polyester film No month/year available.

Abstract of Japanese Patent 0 0531 2761 A2; 1993; Y. Fukuda, et al. No month available.

Cassidy, et al.; "Novel Electrochemical Device for the Detection of Cholesterol or Glucose"; vol. 118; Analyst, Apr. 1993; pp. 415–418.

Reilly, Charles; "Electrochemistry Using Thin–layer Cells"; Rev. Pure and Appl. Chem., vol. 18, 1968; pp 137–151 No month available.

Christensen & Anson; "Chronopotentiometry in Thin Layers of Solution"; Analytical Chemistry; vol. 35; No. 2, 1963, pp. 205–209 No month available.

Hubbard & Anson; "New Electrodes for Chronopotentiometry in Thin Layers of Solution"; Analytical Chemistry; vol. 36, No. 4, Apr. 1964; pp. 723–726.

McDuffie, Anderson, & Reilly; "Twin Electrode Thin–Layer Electrochemistry"; Analytical Chemistry; vol. 38; No. 7; Jun. 1966; pp. 883–890.

Morris, Franta, and White: "Electrochemistry at Pt Band Electrodes of Width Approaching Molecular Dimensions. Breakdown of Transport Equestions at Very Small Electrodes"; The Journal of Physical Chemistry; vol. 91; No. 13; 1987; pp. 3559–3564 No month available.

Nicholson and Shain; "Theory of Stationary Electrode Polarography"; Analytical Chemistry; vol. 36; No. 4, Apr. 1964; pp. 706–723.

Pickup, Kutner, Leidner, and Murray; "Redox Conduction in Single and bilayer Films of Redox Polymer"; American Chem. Society; vol. 106; No. 7; 1984 No month available.

Chidsey, Feldman, Lundgren, and Murray; "Micrometer–Spaced pLATINUM Interdigitated Array Electrode: Fabrication, Theory, and Initial Use"; Analytical Chemistry; vol. 58; No. 3; Mar. 1986;; 801–807.

Anderson, MdDuffi, Reilley; "Diagnostic Criteria for the Study of Chemical and Physical Processes by Twin–Electrode Thin–Layer Electrochemistry"; Journal of Electroanalytical Chemistry; vol. 12; 1966; pp. 477–494 No month available.

Hubbard; "Study of the Kinetics of Electrochemical Reactions by Thin–Layer Voltammetry"; Journal of Electroanalytical Chemistry; vol. 22; 1969; pp. 165–174 No month available.

Anderson and Reilley; "Thin–Layer Electrochemistry: Steady–State Methods of Studying Rate Processes"; vol. 10; 1965; pp. 295–305 No month available.

Specification sheet from Adhesives Research, Inc., ARclad®8314 (May 2, 1997).

Specification sheet from Adhesives Research, Inc., ARcare®4148 (Mar. 30, 1995) (2 pages).

Anderson, et al., Thin–layer electrochemistry: steady–state methods of studying rate processes, *J. Electroanal. Chem.*, 10(1965) 295–305 No month available.

Hubbard, et al., The Theory and Practice of Electrochemistry with Thin Layer Cells, *in Electroanalytical Chemistry*, (Bard Ed.), Marcel Deletier, New York, 1970, vol. 4 (pp. 129–214) No month available.

Derwent Abstract Accession No. 92 119462/15, Class S03, JP,A, 04–62463 (Tokyo Yogyo K.K.) Feb. 27, 1992.

Patent Abstracts of Japan, P–269, p. 166, JP, A,59–3345 (Hitachi Seisakusho K.K.) Jan. 10, 1994.

* cited by examiner

ELECTROCHEMICAL CELL

FIELD OF THE INVENTION

This invention relates to a biosensor and more particularly to an electrochemical biosensor for determining the concentration of an analyte in a carrier. The invention is particularly useful for determining the concentration of glucose in blood and is described herein with reference to that use but it should be understood that the invention is applicable to other analytic determinations.

BACKGROUND OF THE INVENTION

Electrochemical biosensors generally comprise a cell having a working electrode, a counter electrode and a reference electrode. Sometimes the function of the counter and reference electrodes are combined in a single electrode called a "counter/reference" electrode or "pseudo reference electrode". As herein used the term "counter electrode" includes a counter/reference electrode where the context so admits.

The sample containing the analyte is brought into contact with a reagent containing an enzyme and a redox mediator in the cell. Either the mediator is reduced (receives at least one electron) while the analyte is oxidised (donates at least one electron) or visa versa. Usually it is the analyte which is oxidised and the mediator which is reduced. The invention will be herein described principally with reference to that system but it is also applicable to systems in which the analyte is reduced and the mediator oxidised.

Electrochemical glucose analysers such as those used by diabetics to monitor blood glucose levels or such as are used in clinics and hospitals are commonly based upon the use of an enzyme such as glucose oxidase de hydrogenase (GOD) and a redox mediator such as a ferricyanide or ferrocyanide. In such prior art system, the sample (e.g. blood) containing the analyte (e.g. glucose) is brought into contact with the reagents in the cell. Glucose is oxidised to gluconic acid and the glucose oxidase is thereby reduced. The mediator then re-oxidizes the glucose oxidase and is reduced in the process. The reduced mediator is then re-oxidized when it transfers electrons to the working electrode. After allowing passage of a predetermined time, sufficient to obtain an accurate estimate of the Faraday current, the concentration of glucose is estimated from the magnitude of the current or voltage signal then measured.

Prior art electrochemical cells consist of two (or three) adjacent electrodes spaced apart on one side of an insulator and adapted for connection to a measuring device. A target area on which the blood sample is placed is defined on or between the electrodes. Co-pending Application PCT/AU95/00207 describes a cell in which electrodes are disposed on opposite sides of a porous membrane, one of the electrodes having a liquid permeable target area.

In the prior art there is a need to separate the working electrode from the counter (or counter/reference) electrode by a sufficient distance to avoid products of electrochemical reaction at one electrode from interfering with those at the other. In practice a separation of the electrodes of more than 500 $\mu$m is required to achieve acceptable accuracy.

Each batch of cells is required to have been previously calibrated and leads to inaccuracies during use because of variations within the batch, in sample composition, and in ambient conditions.

It is desired to improve the accuracy and reliability of such biosensors. Achievement of these objectives is made difficult in the case of sensors intended to determine the concentration of analytes in blood because blood contains dissolved gases, ions, colloids, complex micelles, small scale cellular debris, and living cellular components in a predominantly aqueous medium. Any of these may interfere in the determination. Existing sensors are also susceptible to influence from other interfering substances that may be present in the sample and which may be oxidised at the working electrode and mistakenly identified as the analyte of interest. Alternatively, the interfering substances may reduce the oxidised form of the redox mediator. These effects will give artificially elevated estimates of the analyte concentration. Additionally there is always some reduced redox mediator present before the analyte is added and its concentration needs to be known and subtracted from the measured value of reduced mediator to give an accurate concentration of the analyte. Moreover, oxygen in the blood may act as a redox mediator for glucose oxidase dehydrogenase (GOD) in competition with ferrocyanide. Thus high oxygen concentrations can lead to low estimates of glucose concentration. In addition the measurements are sensitive to factors such as changes in humidity, temperature, solution viscosity and haematocrit content.

OBJECT OF THE INVENTION

It is an object of the present invention to provide a method of analysis and apparatus for use in the method which avoid or ameliorate at least some of the disadvantages of the prior art. It is an object of preferred forms of the invention to provide a biosensor of improved accuracy, and/or reliability and/or speed and a method for its use.

DISCLOSURE OF THE INVENTION

According to one aspect the invention consists in a method for determining the concentration of a reduced (or oxidised) form of a redox species in an electrochemical cell of the kind comprising a working electrode and a counter electrode spaced from the working electrode by a predetermined distance, said method comprising the steps of:

(1) applying an electric potential difference between the electrodes, (2) selecting the potential of the working electrode such that the rate of electro-oxidation of the reduced form (or electro-reduction of the oxidised form) of the species is diffusion controlled, (3) selecting the spacing between the worldling electrode and the counter electrode so that reaction products from the counter electrode arrive at the working electrode, (4) determining current as a function of time after application of the potential and prior to achievement of a steady state, (5) estimating the magnitude of the steady state current, and (6) obtaining from the change in current with time and the magnitude of the steady state current, a value indicative of the diffusion coefficient and/or of the concentration of the reduced form (or the oxidised form) of the species.

The concentration measured in this way is substantially independent of variation if any in the diffusion coefficient of the reduced form, and therefore is compensated for variations in temperature and viscosity. The concentration so measured is independent of variations in haematocrit and other substances which affect the diffusion coefficient of the reduced form of the redox species.

It will be appreciated that the method of the invention is equally applicable for determining the concentration of a reduced form of a redox species or an oxidized form of a redox species in the cell. In the case that the concentration of the reduced form is to be determined the potential of the working electrode must be maintained such that the rate of electro oxidation of the reduced form is diffusion controlled in step (2) and it is the concentration of the reduced form that is obtained in step (5). In the case that the concentration of oxidized form is to be determined, the potential of the working electrode must be maintained such that the rate of electro reduction of the oxidized form is diffusion controlled in step (2) and it is the concentration of the oxidized form that is obtained in step (5).

The redox species may be an analyte or may be a redox mediator.

In preferred embodiments of the method a mediator is used and the concentration of the reduced (or oxidized) form of the mediator is in turn indicative of the concentration of an analyte and a measure of the diffusion coefficient of the reduced (or oxidized) form of the mediator is determined as a precursor to the determination of the concentration of the analyte.

For preference the cell comprises a working electrode and counter/reference electrode. If a reference electrode separate from a counter electrode is used, then the reference electrode may be in any convenient location in which it is in contact with the sample in the sensor.

In contrast to prior art, when conducting the method of the invention, the electrodes are sufficiently close that the products of electrochemical reaction at the counter electrode migrate to the working electrode during the period of the test. For example, in an enzyme ferricyanide system, the ferrocyanide produced at the counter electrode diffuses to the working electrode.

This allows a steady state concentration profile to be achieved between the electrodes leading to a steady state current. This in turn allows the diffusion coefficient and concentration of the redox species (mediator) to be measured independently of sample variations and therefore greatly improves accuracy and reliability.

The method also permits the haematocrit concentration of blood to be determined from the diffusion coefficient by use of look-up tables (or by separation of red cells from plasma and measurement of the diffusion coefficient of the red cell fraction) and the plasma fraction, and comparing the two.

According to a second aspect, the invention consists in apparatus for determining the concentration of a redox species in an electrochemical cell comprising:

an electrochemical cell having a working electrode and a counter (or counter/reference) electrode, means for applying an electric potential difference between said electrodes, means for measuring the change in current with time, and characterised in that the working electrode is spaced from the counter electrode by less than 500 $\mu$m.

In preferred embodiments the cell has an effective volume of 1.5 microliters or less. Apparatus for use in the invention may comprise a porous membrane, a working electrode on one side of the membrane, a counter/reference electrode on the other side, said electrodes together with a zone of the membrane therebetween defining an electrochemical cell, and wherein the membrane extends laterally from the cell to a sample deposition area spaced apart from the cell zone by a distance greater than the thickness of the membrane.

Preferably the porous membrane, the distance of the target area from the cell portion, and the membrane thickness are so selected in combination that when blood (comprising plasma and red cells) is placed on the target area a plasma front diffuses laterally towards the electrochemical cell zone in advance of the red cells.

It is thus possible to fill a thin layer electrochemical cell with plasma substantially free of haematocrit which would cause a variation in the diffusion coefficient of the redox mediator and which would affect the accuracy of the test as hereinafter explained.

In preferred embodiments of the biosensor according to the invention a second electrochemical cell zone of the membrane is defined by a second working electrode and a second counter/reference electrode on the opposite side of the membrane from the second working electrode. The second electrochemical cell zone is situated intermediate the first cell zone and the sample deposition or "target" area, or is situated on the side of the target area remote from the first electrochemical zone. In these embodiments the plasma comes into contact with enzyme in, or on route to, the first electrochemical cell while plasma reaching the second cell does not. The first cell thus in use measures the concentration of reduced mediator in the presence of plasma (including electrochemically interfering substances), and enzyme while the second electrochemical cell measures it in the presence of plasma (including electrochemically interfering substances) and in the absence of enzyme. This allows determination of the concentration of the reduced interfering substances in the second cell and the concentration of reduced interfering substances plus analyte in the first cell. Subtraction of the one value from the other gives the absolute concentration of analyte.

In a highly preferred embodiment of the invention a hollow cell is employed wherein the working and reference (or counter/reference) electrodes are spaced apart by less than 500 $\mu$m and preferably by from 20–200 $\mu$m.

DESCRIPTION OF THE DRAWINGS

The invention will now be more particularly described by way of example only with reference to the accompanying drawings wherein:

In FIGS. 5 to 12, components corresponding in function to components of the embodiment of FIGS. 1 to 4 are identified by identical numerals or indica.

DESCRIPTION OF PREFERRED EMBODIMENTS

Figure 1:
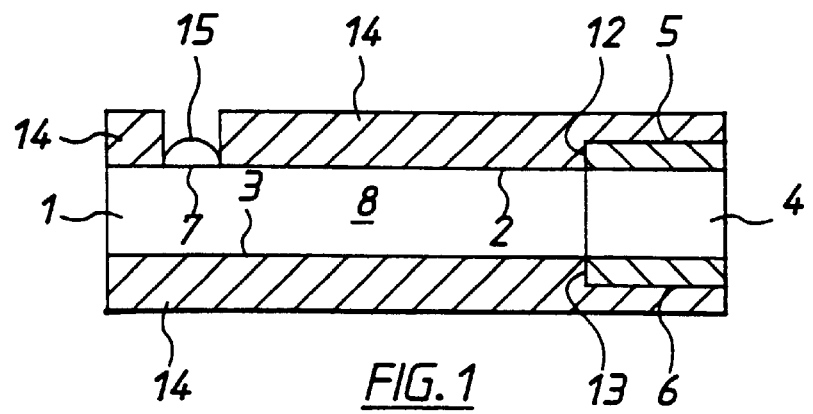
FIG. 1 is a schematic drawing (not to scale) of a first embodiment according to the invention shown in side elevation.
Figure 2:
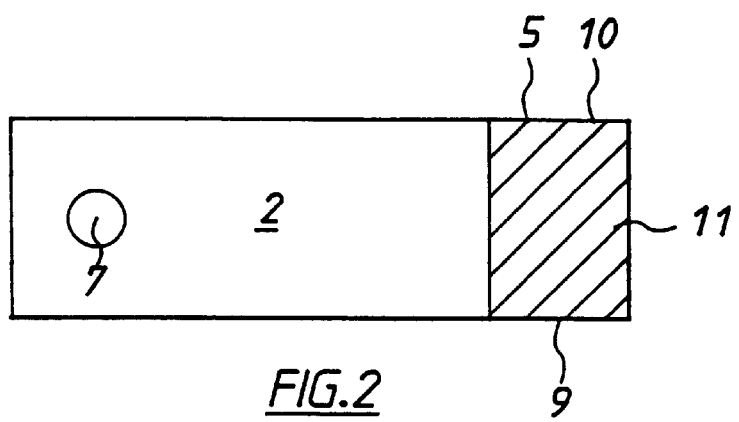
FIG. 2 shows the embodiment of FIG. 1 in plan, viewed from above.
Figure 3:
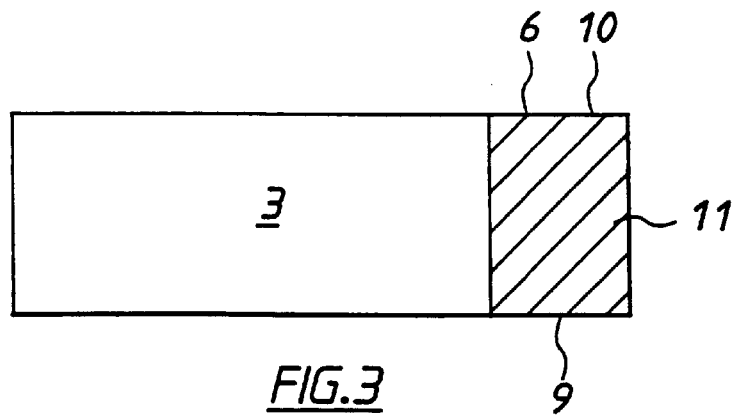
FIG. 3 shows the embodiment of FIG. 1 in plan, viewed from below.
Figure 4:
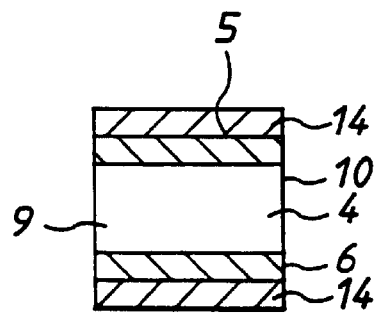
FIG. 4 shows the embodiment of FIG. 1 viewed in end elevation.

With reference to FIGS. 1 to 4 there is shown a first embodiment of apparatus of the invention, in this case a biosensor for determining glucose in blood. The embodiment comprises a thin strip membrane 1 having upper and lower surfaces 2, 3 and having a cell zone 4 defined between a working electrode 5 disposed on upper surface 2 and a counter electrode 6 disposed on lower surface 3. The membrane thickness is selected so that the electrodes are separated by a distance "1" which is sufficiently close that the products of electrochemical reaction at the counter electrode migrate to the working electrode during the time of the test and a steady state diffusion profile is substantially achieved. Typically, "1" will be less than 500 μm. A sample deposition or "target" area 7 defined on upper surface 2 of membrane 1 is spaced at a distance greater than the membrane thickness from cell zone 4. Membrane 1 has a diffusion zone 8 extending between target area 7 and cell zone 4. A suitable reagent including a redox mediator "M", an enzyme "E" and a pF buffer "B" are contained within cell zone 4 of the membrane and/or between cell zone 4 and target area 7. The reagent may also include stabilisers and the like.

In some cases it is preferable to locate the enzyme and mediator and/or the buffer in different zones of the membrane. For example the mediator may be initially located within electrochemical cell zone 4 while the enzyme may be situated below target area 7 or in diffusion zone 8.

Hemoglobin releases oxygen at low pH's, but at higher pH's it binds oxygen very firmly. Oxygen acts as a redox mediator for glucose oxidase dehydrogenase (GOD). In a glucose sensor this competes with the redox mediator leading to low estimates of glucose concentration. Therefore if desired a first pH buffer can be contained in the vicinity of target area 7 to raise the pH to such a level that all the oxygen is bound to hemoglobin. Such a pH would be non-optimal for GOD/glucose kinetics and would consequently be detrimental to the speed and sensitivity of the test. In a preferred embodiment of the invention a second pH buffer is contained as a reagent in the vicinity of the working electrode to restore the pH to kinematically optimal levels. The use of a second buffer does not cause oxygen to be released from the hemoglobin as the hemoglobin is contained within the blood cells which are retained near blood target area 7 or are retarded in diffusion in comparison with the plasma and therefore not influenced by the second buffer. In this manner oxygen interference may be greatly reduced or eliminated.

In use of the sensor a drop of blood containing a concentration of glucose to be determined is placed on target zone 7. The blood components wick towards cell zone 4, the plasma component diffusing more rapidly than red blood cells so that a plasma front reaches cell zone 4 in advance of blood cells.

When the plasma wicks into contact with the reagent, the reagent is dissolved and a reaction occurs that oxidises the analyte and reduces the mediator. After allowing a predetermined time to complete this reaction an electric potential difference is applied between the working electrode and the counter electrode. The potential of the working electrode is kept sufficiently anodic such that the rate of electro oxidation of the reduced form of the mediator at the working electrode is determined by the rate of diffusion of the reduced form of the mediator to the working electrode, and not by the rate of electron transfer across the electrode/solution interface.

In addition the concentration of the oxidised form of the mediator at the counter electrode is maintained at a level sufficient to ensure that when a current flows in the electrochemical cell the potential of the counter electrode, and thus also the potential of the working electrode, is not shifted so far in the cathodic direction that the potential of the working electrode is no longer in the diffusion controlled region. That is to say, the concentration of the oxidized form at the counter electrode must be sufficient to maintain diffusion controlled electro oxidation of the reduced form of the mediator at the working electrode.

The behaviour of a thin layer cell is such that if both oxidised and reduced forms of the redox couple are present, eventually a steady state concentration profile is established across the cell. This results in a steady state current. It has been found that by comparing a measure of the steady state current with the rate at which the current varies in the current transient before the steady state is achieved, the diffusion coefficient of the redox mediator can be measured as well as its concentration. This is in contrast to the Cottrell current that is measured in the prior art. By measuring the Cottrell current at known times after application of a potential to the sensor electrodes it is only possible to determine the product concentration times square root of the diffusion coefficient and therefore it is not possible to determine the concentration of the mediator independent of its diffusion coefficient.

In a cell according to the current invention, by solving the appropriate diffusion equations it can be shown that over a restricted time range a plot of $\ln(i/i^\infty - 1)$ vs time (measured in seconds) is linear and has a slope (denoted by S) which is equal to $-4\pi^2 D/l^2$, where "i" is the current at time "t", "$i^\infty$" is the steady state current, "D" is the diffusion coefficient in $cm^2/sec$, "1" is the distance between the electrodes in cm and "π" is approximately 3.14159. The concentration of reduced mediator present when the potential was applied between the electrodes is given by $2\pi^2 i^\infty/FA1S$, where "F" is Faraday's constant, A is the working electrode area and the other symbols are as given above. As this later formula uses S it includes the remeasured value of the diffusion coefficient.

Since 1 is a constant for a given cell, measurement of i as a function of time and $i^\infty$ enable the value of the diffusion coefficient of the redox mediator to be calculated and the concentration of the analyte to be determined.

Moreover the determination of analyte concentration compensates for any variation to the diffusion coefficient of the species which is electro oxidised or electro reduced at the working electrode. Changes in the value of the diffusion coefficient may occur as a result of changes in the temperature and viscosity of the solution or variation of the membrane permeability. Other adjustments to the measured value of the concentration may be necessary to account for other factors such as changes to the cell geometry, changes to the enzyme chemistry or other factors which may effect the measured concentration. If the measurement is made con plasma substantially free of haematocrit (which if present causes variation in the diffusion coefficient of the redox mediator) the accuracy of the method is further improved.

Each of electrodes 5, 6 has a predefined area. In the embodiments of FIGS. 1 to 4 cell zone 4 is defined by edges 9, 10, 11 of the membrane which correspond with edges of electrodes 5, 6 and by leading (with respect to target area 7)

edges 12, 13 of the electrodes. In the present example the electrodes are about 600 angstrom thick and are from 1 to 5 mm wide.

Optionally, both sides of the membrane are covered with the exception of the target area 7 by laminating layers 14 (omitted from plan views) which serves to prevent evaporation of water from the sample and to provide mechanical robustness to the apparatus. Evaporation of water is undesirable as it concentrates the sample, allows the electrodes to dry out, and allows the solution to cool, affecting the diffusion coefficient and slowing the enzyme kinetics, although diffusion coefficient can be estimated as above.

Figure 5:
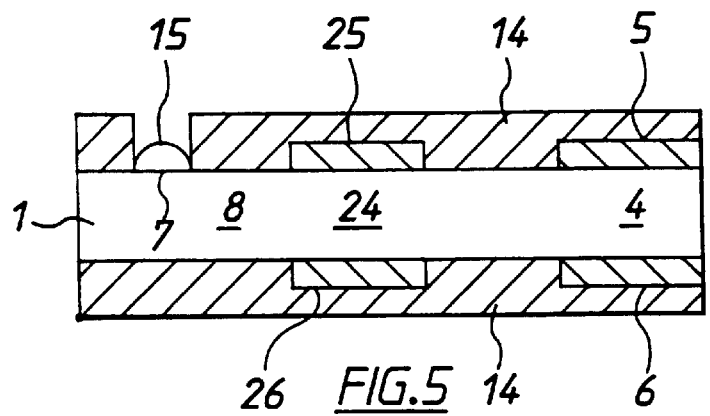
FIG. 5 is a schematic drawing (not to scale) of a second embodiment according to the invention in side elevation.
Figure 6:
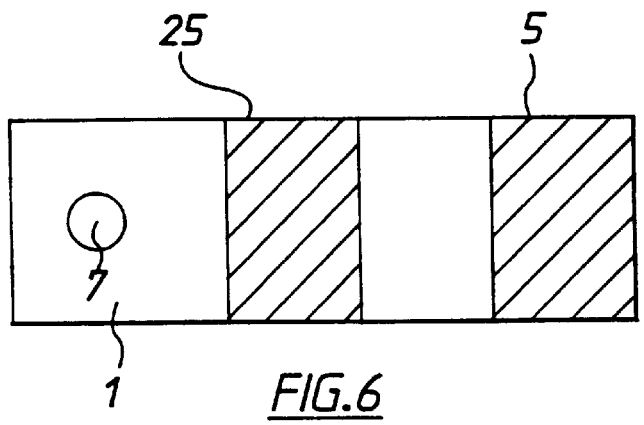
FIG. 6 shows the embodiment of FIG. 5 in plan, viewed from above.

A second embodiment according to the invention, shown in FIGS. 5 and 6, differs from the first embodiment by inclusion of a second working electrode 25 and counter/reference electrode 26 defining a second cell zone 24 therebetween. These electrodes are also spaced apart by less than 500 $\mu$m in the present example. Second electrodes 25, 26 are situated intermediate cell zone 4 and target area 7. In this embodiment the redox mediator is contained in the membrane below or adjacent to target area 7 or intermediate target area 7 and first cell zone 4. The enzyme is contained in the membrane in the first cell zone 4 and second cell zone 24. The enzyme does not extend into second cell 24. In this case when blood is added to the target area, it dissolves the redox mediator. This wicks along the membrane so that second electrochemical cell 24 contains redox mediator analyte and serum including electrochemically interfering substances. First electrochemical cell receives mediator, analyte, serum containing electrochemically interfering substances, and enzyme. Potential is now applied between both working electrodes and the counter electrode or electrodes but the change in current with time is measured separately for each pair. This allows the determination of the concentration of reduced mediator in the absence of analyte plus the concentration of electrochemically interfering substances in the second electrochemical cell and the concentration of these plus analyte in the first electrochemical cell. Subtraction of the one value from the other gives the absolute concentration of analyte.

Figure 7:
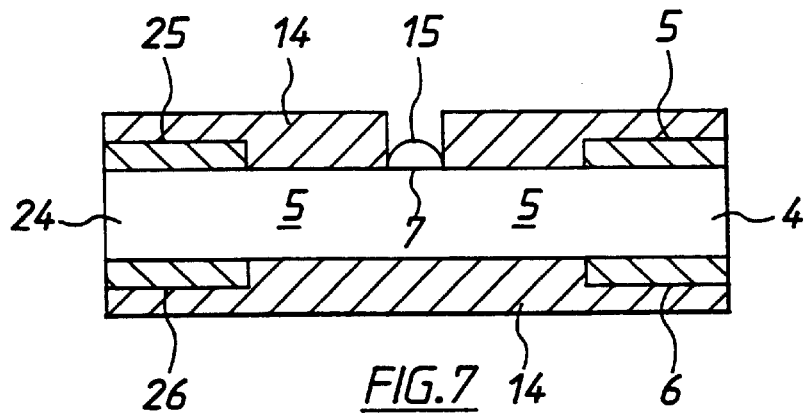
FIG. 7 is a schematic drawing (not to scale) of a third embodiment according to the invention, in side elevation.
Figure 8:
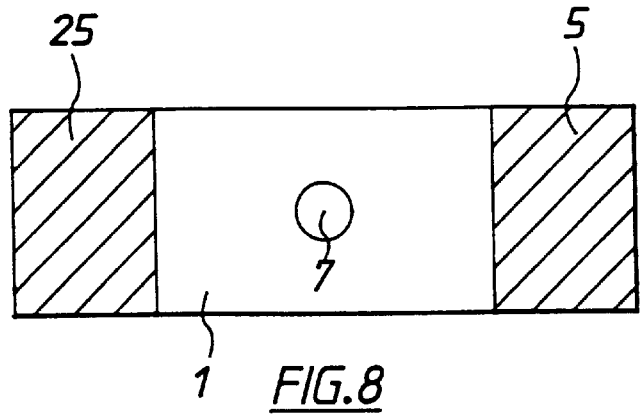
FIG. 8 shows the embodiment of FIG. 7 in plan, viewed from above.

The same benefit is achieved by a different geometry in the embodiment of FIGS. 7 and 8 in which the second working electrode and second counter/reference electrode define the second cell 24 on the side of target area 7 remote from first electrochemical cell 4. In this case the enzyme may be contained in the membrane strip between the target area and cell 1. The redox mediator may be in the vicinity of the target area or between the target area and each cell. The diffusion coefficient of mediator is lowered by undissolved enzyme and the arrangement of FIGS. 7 and 8 has the advantage of keeping enzyme out of the thin layer cells and allowing a faster test (as the steady state current is reached more quickly). Furthermore the diffusion constant of redox mediator is then the same in both thin layer cells allowing more accurate subtraction of interference.

Figure 9:
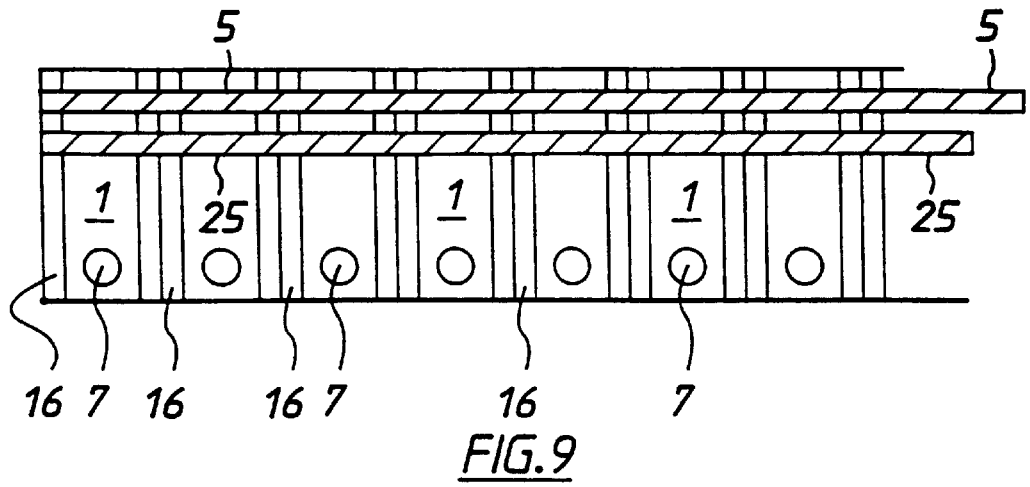
FIG. 9 is a schematic drawing (not to scale) according to the invention in plan view, viewed from above.
Figure 10:
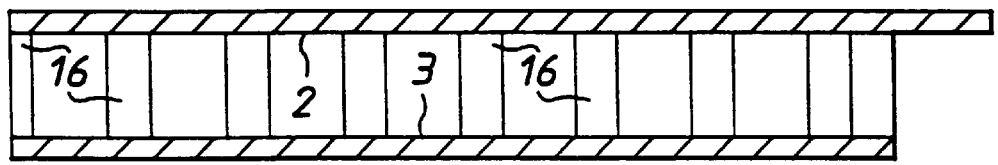
FIG. 10 shows the embodiment of FIG. 9 in mind elevation.
Figure 11:
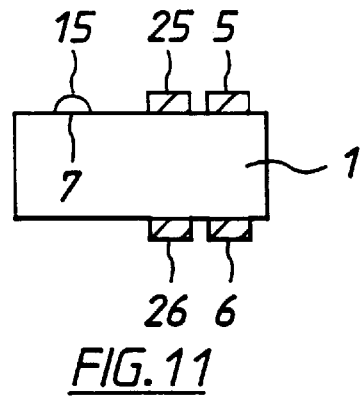
FIG. 11 shows the embodiment of FIG. 9 in side elevation.

Although the embodiments of FIGS. 1 to 8 are unitary sensors, it will be understood that a plurality of sensors may be formed on a single membrane as shown in the embodiment of FIGS. 9 to 11. In this case the electrodes of one sensor are conductively connected to those of an adjacent sensor. Sensors may be used successively and severed from the strip after use.

In the embodiment of FIGS. 9 to 11 electrode dimensions are defined in the diffusion direction (indicated by arrow) by the width of the electrode in that direction. The effective dimension of the electrode in a direction transverse to diffusion direction is defined between compressed volumes 16 of the membrane in a manner more fully described in co-pending Application PCT/AU96/00210, the disclosure of which is incorporated herein by reference in its entirety. For clarity optional laminated layer 14 of FIG. 1 has been omitted from FIGS. 9 to 11.

Figure 12:
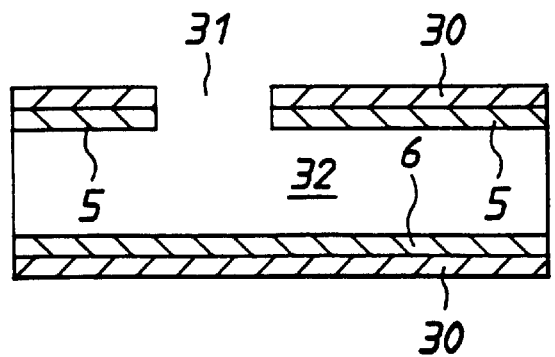
FIG. 12 shows a schematic drawing (not to scale) of a hollow cell embodiment according to the invention, viewed in cross section.

In the embodiment of FIG. 12 there is shown a hollow cell according to the invention wherein the electrodes 5, 6 are supported by spaced apart polymer walls 30 to define a hollow cell. An opening 31 is provided on one side of the cell whereby a sample can be admitted into cavity 32. In this embodiment a membrane is not used. As in previous embodiments, the electrodes are spaced apart by less than 500 $\mu$m, preferably 20–400 $\mu$m and more preferably 20–200 $\mu$m. Desirably the effective cell volume is 1.5 microliters or less.

It will be understood that the method of the invention may be performed with a cell constructed in accord with co-pending application PCT/AU95/00207 or cells of other known design, provided these are modified to provide a sufficiently small distance between electrode faces.

Figure 13:
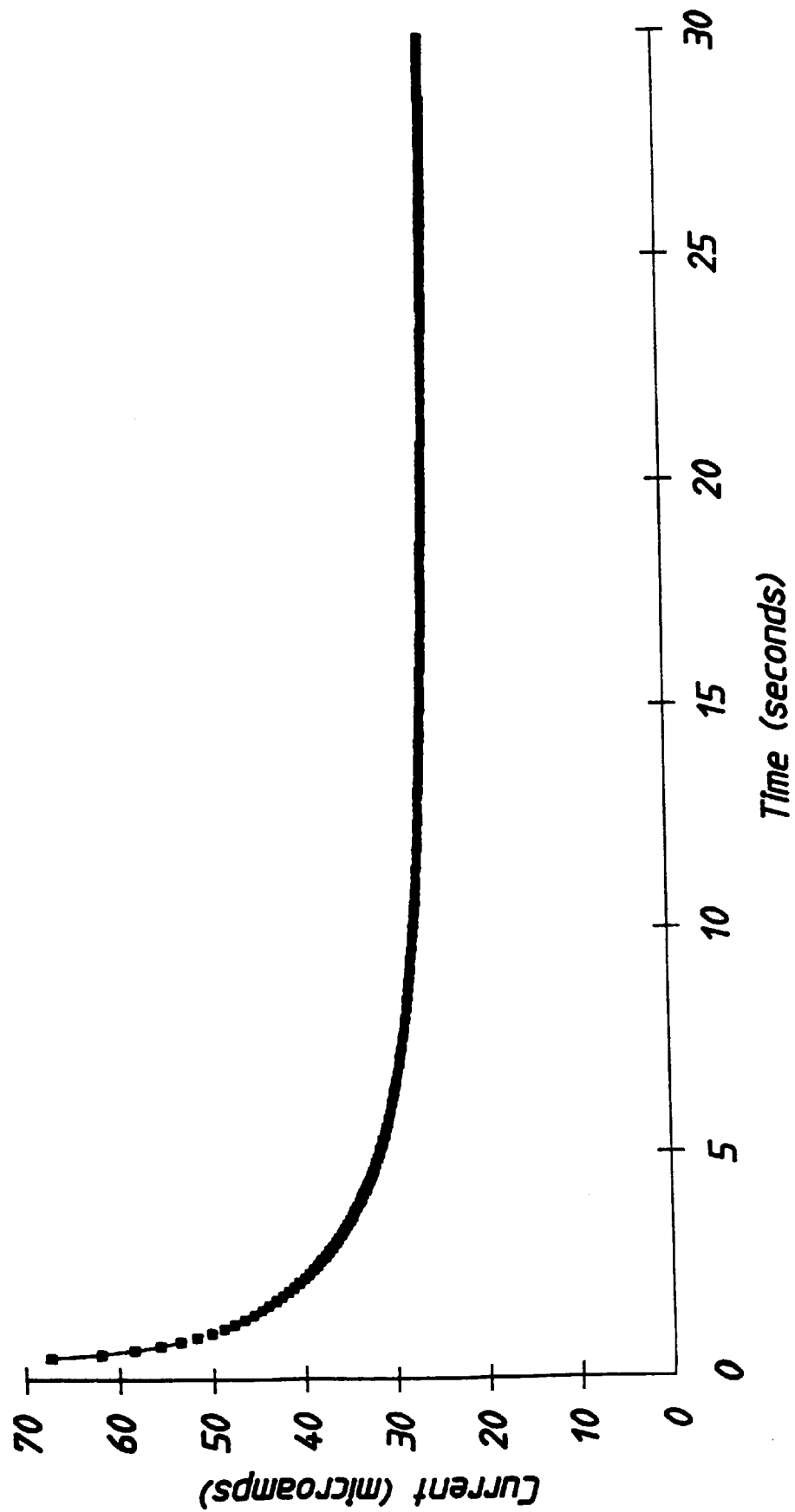
FIG. 13 is a graph showing a plot of current (ordinate axis) versus time (co-ordinate axis) during conduct of a method according to the invention.
Figure 14:
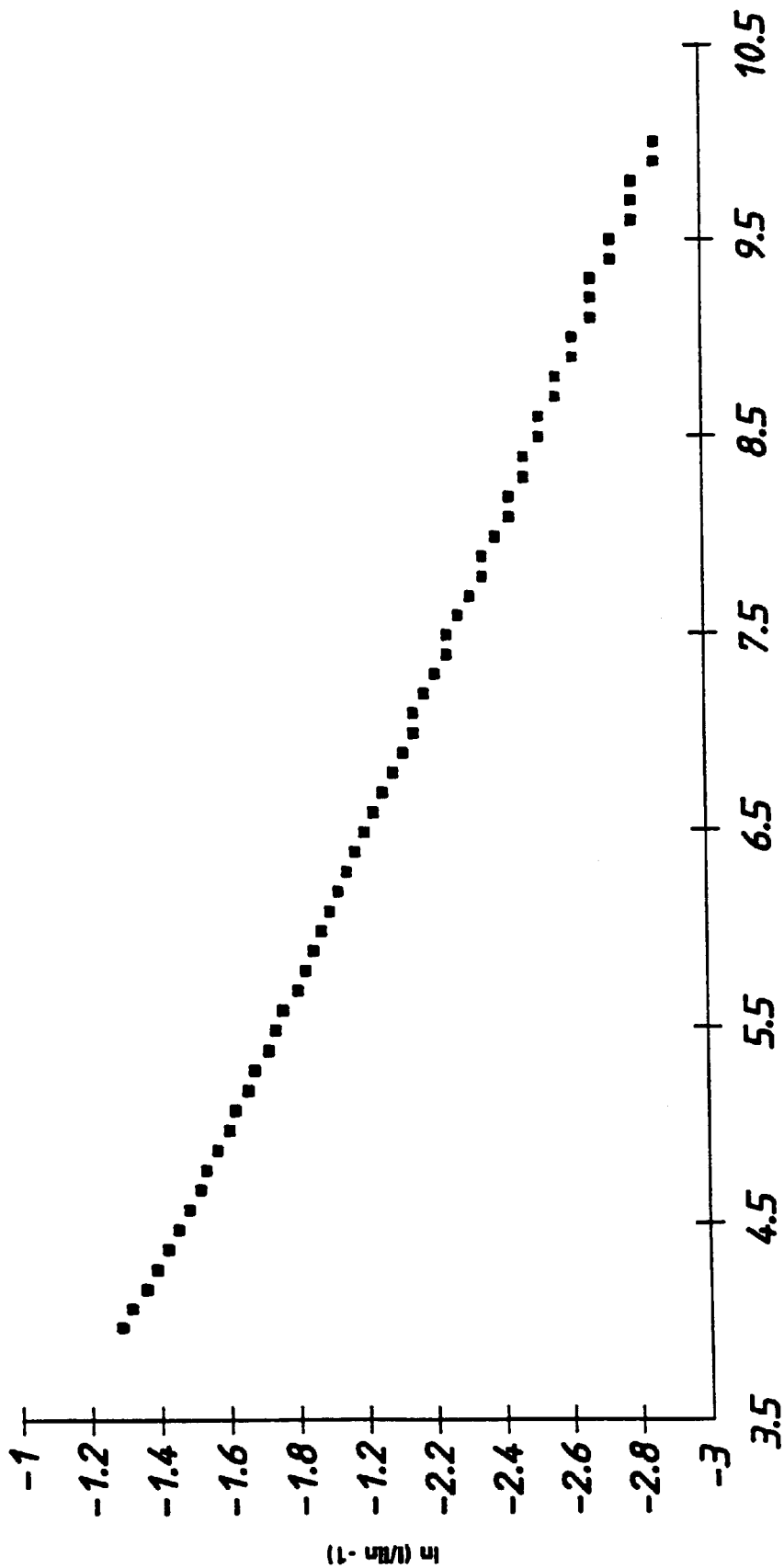
FIG. 14 is a further graph of use in explaining the method of the invention.

The method of the invention will now be further exemplified with reference to FIGS. 13 and 14.

EXAMPLE 1

A membrane 130 microns thick was coated on both sides with a layer of Platinum 60 nanometers thick. An area of 12.6 sq. mm was defined by compressing the membrane. 1.5 microliters of a solution containing 0.2 Molar potassium ferricyanide and 1% by weight glucose oxidase dehydrogenase was added to the defined area of the membrane and the water allowed to evaporate.

The platinum layers were then connected to a potentiostat to be used as the working and counter/reference electrodes. 3.0 microliters of an aqueous solution containing 5 millimolar D-glucose and 0.9 wt % NaCl was dropped on to the defined area of the membrane. After an elapse of 20 seconds a voltage of 300 millivolts was applied between the working and counter/reference electrodes and the current recorded for a further 30 seconds at intervals of 0.1 seconds.

FIG. 13 is a graph of current versus time based on the above measurements. Using a value of the steady state current of 26.9 microamps the function ln(i/26.9−1) was computed and plotted versus time. The slope of the graph (FIG. 14) is −0.342 which corresponds to a diffusion coefficient of $1.5 \times 10^{-6}$ cm$^2$ per second and a corrected glucose concentration (subtracting background ferroc,lanide) of 5.0 millimolar.

The steady state current is one in which no further significant current change occurs during the test. As will be understood by those skilled in the art, a minimum current may be reached after which there may be a drift due to factors such as lateral diffusion, evaporation, interfering electrochemical reactions or the like. However, in practice it is not difficult to estimate the "steady state" current ($i^\infty$). One method for doing so involves approximating an initial value for $i^\infty$. Using the fit of the i versus t data to the theoretical curve a better estimate of $i^\infty$ is then obtained. This is repeated reiteratively until the measured value and approximated. value converge to within an acceptable difference, thus yielding an estimated $i^\infty$.

In practice, the measurements of current i at time t are made between a minimum time t min and a maximum time t max after the potential is applied. The minimum and maximum time are determined by the applicability of tile equations and can readily be determined by experiment of a routine nature. If desired the test may be repeated by switching off the voltage and allowing the concentration profiles of the redox species to return towards their initial states.

It is to be understood that the analysis of the current v. time curve to obtain values of the Diffusion Co-efficient and/or concentration is not limited to the method given above but could also be achieved by other methods.

It will be understood that in practice of the invention an electrical signal is issued by the apparatus which is indicative of change in current with time. The signal may be an analogue or digital signal or may be a series of signals issued at predetermined time intervals. These signals may be processed by means of a microprocessor or other conventional circuit to perform the required calculations in accordance with stored algorithms to yield an output signal indicative of the diffusion coefficient, analyte concentration, haematocrit concentration or the like respectively. One or more such output signals may be displayed by means of an analogue or digital display.

It is also possible by suitable cell design to operate the cell as a depletion cell measuring the current required to deplete the mediator. For example in the embodiment of FIG. 5 the method of the invention may be performed using electrodes 5, 6, which are spaced apart by less than 500 $\mu$m. An amperometric or voltammetric depletion measurement may be made using electrodes 5 and 26 which are spaced apart more than 500 $\mu$m and such that there is no interference between the redox species being amperometrically determined at electrodes 5, 26.

The depletion measurement may be made prior to, during or subsequent to, the measurement of diffusion coefficient by the method of the invention. This enables a substantial improvement in accuracy and reproducability to be obtained.

In the embodiments described the membrane i, preferably an asymmetric porous membrane of the kind described in U.S. Pat. Nos. 4,629,563 and 4,774,039 both of which are incorporated herein in their entirety by reference. However symmetrical porous membranes may be employed. The membrane may be in the form of a sheet, tube, hollow fibre or other suitable form.

If the membrane is asymmetric the target area is preferably on the more open side of the asymmetric membrane. The uncompressed membrane desirably has a thickness of from 20 to 500 $\mu$m. The minimum thickness is selected having regard to speed, sensitivity, accuracy and cost. If desired a gel may be employed to separate haematocrit from GOD. The gel may be present between the electrodes and/or in the space between the sample application area and the electrodes.

The working electrode is of any suitable metal for example gold, silver, platinum, palladium, iridium, lead, a suitable alloy. The working electrode may be preformed or formed in situ by any suitable method for example sputtering, evaporation under partial vacuum, by electrodeless plating, electroplating, or the like. Suitable non-metal conductors may also be used for electrode construction. For example, conducting polymers such as poly(pyrrole), poly (aniline), porphyrin "wires", poly(isoprene) and poly (cis-butadiene) doped with iodine and "ladder polymers". Other non-metal electrodes may be graphite or carbon mixed with a binder, or a carbon filled plastic. Inorganic electrodes such as $In_2O_3$ or $SnO_2$ may also be used. The counter/reference electrode may for example be of similar construction to the working electrode. Nickel hydroxide or a silver halide may also be used to form the counter/reference electrode. Silver chloride may be employed but it will be understood that chloridisation may not be necessary and silver may be used if sufficient chloride ions are present in the blood sample. Although in the embodiments described the working electrode is shown on the upper surface of the biosensor and the counter/reference electrode is on the lower surface, these may be reversed.

It is preferable that the working electrode and counter (or counter/reference) electrodes are of substantially the same effective geometric area.

If a separate reference and counter electrode are employed, they may be of similar construction. The reference electrode can be in any suitable location.

It will be understood that the features of one embodiment hereindescribed may be combined with those of another. The invention is not limited to use with any particular combination of enzyme and mediator and combinations such as are described in EP 0351892 or elsewhere may be employed. The system may be used to determine analytes other than glucose (for example, cholesterol) by suitable adaptation of reagents and by appropriate membrane selection. The system may also be adapted for use with media other than blood. For example the method may be employed to determine the concentration of contaminants such as chlorine, iron, lead, cadmium, copper, etc., in water.

Although the cells herein described have generally planar and parallel electrodes it will be understood that other configurations may be employed, for example one electrode could be a rod or needle and the other a concentric sleeve.

It will be apparent to those skilled in the art from the disclosure hereof the invention may be embodied in other forms without departing from the inventive concept herein disclosed.

What is claimed is:

1. A method for determining the concentration of a reduced or oxidized form of a redox species, said method comprising the steps of:

(1) providing an electrochemical cell comprising a working electrode and a counter electrode, (2) applying an electric potential difference between the electrodes, (3) selecting the potential of the working, electrode such that the rate of electro-oxidation of the reduced form or electro-reduction of the oxidized form of the species is diffusion controlled, (4) selecting the spacing between the working electrode and the counter electrode so that reaction products from the counter electrode arrive at the working electrode, (5) determining current as a function of time after application of the potential and prior to achievement of a steady state, (6) estimating the magnitude of the steady state current, and (7) obtaining from the change in current with time and the magnitude of the steady state current, a value indicative of the diffusion coefficient and/or of the concentration of the reduced form or the oxidized fonn of the species.

2. A method according to claim 1 wherein a steady state concentration profile of electrochemical reaction products is achieved between the working electrode and counter electrode during the period of a test.

3. A method according to claim 1 wherein the electrodes are separated by less than 500 $\mu$m.

4. A method according to claim 1 wherein the redox species is a mediator and the concentration of the reduced or oxidized form of the mediator is indicative of the concentration of an analyte and wherein a measure of the diffusion coefficient of the reduced or oxidized form of the mediator is determined as a precursor to the determination of the concentration of the analyte.

5. A method according to claim 1 wherein the steady state current is estimated by approximating an initial value for the steady state current, measuring a discrepancy between measured current versus time data and a theoretical curve, and using the degree of discrepancy, if any, to obtain a better estimate of the steady state current.

6. A method according to claim 1 wherein the redox species is an analyte.

7. A method according to claim 1 wherein the redox is a mediator.

8. A method according to claim 1 wherein the electrochemical cell additionally comprises a separate reference electrode.

9. A method according to claim 1 wherein the spacing between the electrodes is selected such what the steady state current is achieved within a desired time.

10. A method according to claim 1 when used for determining haematocrit level.

11. A method according to claim 1 when used to determine the concentration of glucose in blood.

12. Apparatus comprising a porous membrane, a working electrode on one side of the membrane, a counter electrode on the other side of the membrane, said electrodes together with a zone of the membrane therebetween defining an electrochemical cell, and wherein the membrane extends laterally from the cell to a sample deposition area spaced apart from the cell zone by a distance greater than the thickness of the membrane, wherein the distamce is sufficient so that when blood is placed on the sample deposition area, a plasma front diffuses laterally towards the cell zone in advance of the red cells, filling the cell area with plasma substantially free of hematocrit.

13. Apparatus according to claim 12 wherein the electrochemical cell contains a reagent.

14. Apparatus according to claim 12 wherein the electrochemical cell contains a mediator.

15. Apparatus according to claim 12 wherein the membrane contains an enzyme intermediate the electrochemical cell and the sample deposition area.

16. Apparatus according to claim 12 further comprising a pH buffer in the vicinity of the sample deposition area.

17. Apparatus according to claim 12 further comprising a pH buffer in the vicinity of the working electrode.

18. Apparatus according to claim 12 comprising a second electrochemical cell zone of the membrane defined by a second working electrode anda second counter/reference electrode on the opposite side of the membrane from the second working electrode.

19. Apparatus according to claim 18 wherein the second electrochemical cell zone is situated intermediate the first cell zone and the sample deposition or target area.

20. Apparatus according to claim 12 wherein the uncompressed membrane has a thickness of less than 500 $\mu$m.

21. Apparatus according to claim 12 wherein the working electrode is a metal selected from the group comprising gold, silver, platinum, palladium, iridium, lead and alloys thereof.

22. Apparatus according to claim 12 for use in measuring the concentration of glucose in blood.

23. Apparatus for determining the concentration of a redox species in an electrochemical cell comprising:

a hollow electrochemical cell having a working electrode and a counter or counter/reference electrode, means for applying an electric potential difference between said electrodes, means for measuring the change in current with time, and characterised in that the working electrode is spaced from the counter electrode by less than 500 $\mu$m.

24. An electrochemical cell according to claim 23 wherein the electrodes are spaced from 100–200 $\mu$m apart.

25. An electrochemical cell according to claim 23 wherein the electrodes are facing one another.

26. An electrochemical cell according to claim 23 wherein the electrodes are of substantially corresponding area.

27. An electrochemical cell according to claim 23 comprising a working electrode, a counter electrode and a separate reference electrode.

28. An electrochemical cell according to claim 23 having an effective cell volume of less than 1.5 microlitres.

29. Apparatus according to claim 23 for use in measuring the concentration of glucose in blood.

30. The apparatus according to claim 23, wherein the working electrode is preformed.

31. The apparatus according to claim 23, wherein the working electrode comprises a non-metal.

32. The apparatus according to claim 31, wherein the non-metal is selected from the group consisting of graphite, carbon mixed with a binder, and carbon-filled plastic.

33. The apparatus according to claim 23, wherein the counter or counter/reference electrode is preformed.

34. The apparatus according to claim 23, wherein the counter or counter/reference electrode comprises a metal selected from the group consisting of gold, silver, platinum, palladium, iridium, lead and alloys thereof.

35. The apparatus according to claim 23, wherein the counter or counter/reference electrode comprises a non-metal.

36. The apparatus according to claim 35, wherein the non-metal is selected from the group consisting of graphite, carbon mixed with a binder, and carbon-filled plastic.

37. The apparatus according to claim 23, wherein the counter or counter/reference electrode comprises silver halide.

38. The apparatus according to claim 23, wherein the counter or counter/reference electrode comprises silver, and wherein the reduced or oxidized fonn of the redox species is contained within a sample comprising chloride ions.

39. The apparatus according to claim 23, wherein the hollow electrochemical cell has at least one wall.

40. The apparatus according to claim 39, wherein the wall comprises a polymer.

41. The apparatus according to claim 23, wherein the electrodes are spaced apart by about 20 $\mu$m to about 400 $\mu$m.

42. The apparatus according to claim 41, wherein the electrodes are spaced apart by about 20 $\mu$m to about 200 $\mu$m.

43. The apparatus according to claim 42, wherein the electrodes are spaced apart by about 100 $\mu$m to about 200 m.

44. The apparatus according to claim 23, wherein the electrodes are spaced apart by about 10 $\mu$m to about 200 $\mu$m.

45. The apparatus according to claim 44, wherein the electrodes are spaced apart by about 60 $\mu$m to about 120 $\mu$m.

46. The apparatus according to claim 23, wherein the working electrode is about 60 $\mu$m thick.

47. The apparatus according to claim 23, wherein the counter or counter/refercnce electrode is about 60 $\mu$m thick.

48. The apparatus according to claim 23, wherein the electrochemical cell further comprises a mediator.

49. The apparatus according to claim 23, wherein the electrochemical cell further comprises a reagent.

50. The apparatus according to claim 49, wherein the reagent comprises glucose oxidase dehydrogenase.

51. The apparatus according to claim 23, wherein the working electrode has a width of from about 1 μm to about 5 μm.

52. The apparatus according to claim 23, wherein the counter/reference electrode has a width of from about 1 μm to about 5 μm.

53. The apparatus of claim 23, wherein the working electrode and the counter or counter/reference electrode are substantially parallel and substantially opposed.

54. The apparatus according to claim 23, wherein the hollow electrochemical cell further comprises a pH buffer.

55. The apparatus according to claim 23, wherein the redox species is a mediator and a concentration of a reduced or oxidized formi of the mediator is indicative of a concentration of an analyte.

56. The apparatus according to claim 55, wherein the analyte comprises glucose.

57. The apparatus of claim 23, further comprising a glucose sensor, wherein the glucose sensor comprises the electrochemical cell.

58. The apparatus of claim 57, wherein the electrochemical cell has an effective cell volume of less than about 1.5 microliters.

59. The apparatus of claim 57, wherein the electrodes are spaced apart by about 20 μm to about 200 μm.

60. The apparatus of claim 57, wherein the electrochemical cell further comprises a mediator.

61. The apparatus of claim 57, wherein the electrochemical cell further comprises a reagent.

62. The apparatus of claim 61, wherein the reagent comprises glucose oxidase dehydrogenase.

63. The apparatus of claim 57, wherein the electrochemical cell further comprises a pH buffer.

64. The apparatus of claim 57, wherein the working electrode and the counter or counter/reference electrode are substantially parallel and substantially opposed.

65. A hollow electrochemical cell comprising a working electrode, a counter electrode and an opening for admitting an analyte to the cell, the working electrode being spaced from the counter electrode by less than 500 μm.

66. An electrochemical cell according to claim 65 wherein the electrodes are spaced from 100–200 μm apart.

67. An electrochemical cell according to claim 65 wherein the electrodes are facing one another.

68. An electrochemical cell according to claim 65 wherein the electrodes are of substantially corresponding area.

69. An electrochemical cell according to claim 65 comprising a working electrode, a counter electrode and a separate reference electrode.

70. An electrochemical cell according to claim 65 having an effective cell volume of less than 1.5 microlitres.

71. Apparatus according to claim 65 for use in measuring the concentration of glucose in blood.

72. The hollow electrochemical cell according to claim 65, wherein the working electrode is preformed.

73. The hollow electrochemical cell according to claim 65, wherein the working electrode comprises a non-metal.

74. The hollow electrochemical cell according to claim 73, wherein the nonmetal is selected from the group consisting of graphite, carbon mixed with a binder, and carbon-filled plastic.

75. The hollow electrochemical cell according to claim 65, wherein the counter electrode is prefonned.

76. The hollow electrochemical cell according to claim 65, wherein the counter electrode comprises a metal selected from the group consisting of gold, silver, platinum, palladium, iridium, lead and alloys thereof.

77. The hollow electrochemical cell according to claim 65, wherein the counter electrode comprises a non-metal.

78. The hollow electrochemical cell accoirding to claim 77, wherein the nonmetal is selected from the group consisting of graphite, carbon mixed with a binder, and carbon-filled plastic.

79. The hollow electrochemical cell according to claim 65, wherein the counter electrode comprises silver halide.

80. The hollow electrochemical cell according to claim 65, further comprising a redox species capable of existing in a reduced form or an oxidized fonn.

81. The hollow electrochemical cell according to claim 80, wherein the redox species is a mediator and a concentration of the reduced or oxidized form of the mediator is indicative of a concentration of an analyte.

82. The hollow electrochemical cell according to claim 81, wherein the analyte comprises glucose.

83. The hollow electrochemical cell according to claim 80, wherein the counter electrode comprises silver, and wherein the reduced or oxidized form of the redox species is contained within a sample comprising chloride ions.

84. The hollow electrochemical cell according to claim 80, wherein the redox species is selected from the group consisting of chlorine, iron, lead, cadmium, and copper.

85. The hollow electrochemical cell aci.ording to claim 65, wherein the hollow clectrochemical cell has at least one wall.

86. The hollow electrochemical cell according to claim 85, wherein the wall comprises a polymer.

87. The hollow electrochemical cell according to claim 65, wherein the electrodes are spaced apart by about 20 μm to about 400 μm.

88. The hollow electrochemical cell according to claim 87, wherein the electrodes arc spaced apart by about 20 μm to about 200 μm.

89. The hollow electrochemical cell according to claim 88, wherein the electrodes are spaced apart by about 100 μm to about 200 μm.

90. The hollow electrochemical cell according to claim 65, wherein the electrodes are spaced apart by about 10 μm to about 200 μm.

91. The hollow electrochemical cell according to claim 90, wherein the electrodes are spaced apart by about 60 μm to about 120 μm.

92. The hollow electrochemical cell according to claim 65, wherein the working electrode is about 60 μm thick.

93. The hollow electrochemical cell according to claim 65, wherein the counter electrode is about 60 μm thick.

94. The hollow electrochemical cell according to claim 65, wherein the electrochemical cell further comprises a mediator.

95. The hollow electrochemical cell according to claim 65, wherein the electrochemical cell further comprises a reagent.

96. The hollow electrochemical cell according to claim 95, wherein the reagent comprises glucose oxidase dehydrogenase.

97. The hollow electrochemical cell according to claim 65, wherein the working electrode has a width of from 1 mm to 5 mm.

98. The hollow electrochemical cell according to claim 65, wherein the counter electrode has a width of from 1 mm to 5 mm.

99. The electrochemical cell of claim 65, wherein the working electrode and the counter electrode are substantially parallel and substantially opposed.

100. The hollow electrochemical cell according to claim 65, wherein the electrochemical cell further comprises a pH buffer.

101. A glucose sensor comprising the hollow electrochemical cell according to claim 65.

102. The glucose sensor of claim 101, wherein the electrochemical cell has an effective cell volume of less than about 1.5 microliters.

103. The glucose sensor of claim 101, wherein the electrodes are spaced apart by about 20 µm to about 200 µm.

104. The glucose sensor of claim 101, wherein the electrochemical cell further comprises a mediator.

105. The glucose sensor of claim 101, wherein the electrochemical cell further comprises a reagent.

106. The glucose sensor of claim 105, wherein the reagent comprises glucose oxidase dehydrogenase.

107. The glucose sensor of claim 101, wherein the electrochemical cell flirther comprises a pH buffer.

108. The glucose sensor of claim 101, wherein the working electrode and the counter electrode are substantially parallel and substantially opposed.

* * * * *

UNITED STATES PATENT AND TRADEMARK OFFICE
CERTIFICATE OF CORRECTION

PATENT NO.    : 6,284,125 B1                                        Page 1 of 1
DATED         : September 4, 2001
INVENTOR(S)   : Alastair McIndoe Hodges, Thomas William Beck and Oddvar Johansen It is certified that error appears in the above-identified patent and that said Letters Patent is hereby corrected as shown below:

<u>Title page,</u>
Item [56], U.S. PATENT DOCUMENTS,
The U.S. PATENT DOCUMENTS, number reading "5,243,526" is corrected to read
-- 5,243,516 --.

Signed and Sealed this

Seventh Day of May, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,284,125 B1
DATED : September 4, 2001
INVENTOR(S) : Alastair McIndoe Hodges, Thomas William Beck and Oddvar Johansen It is certified that error appears in the above-identified patent and that said Letters Patent is hereby corrected as shown below:

Column 1,
Line 33, please change "de hydrogenase" to -- dehydrogenase --.

Column 2,
Line 46, please change "worldling" to -- working --.

Column 5,
Line 5, please change "indica" to -- indicia --.
Line 27, please change "pF buffer" to -- pH buffer --.
Line 36, please change "Hemoglobin" to -- Haemoglobin --.
Lines 43 and 50, please change "hemoglobin" to -- haemoglobin --.
Line 47, please change "kinematically" to -- kinetically --.

Column 6,
Line 44, please change "remeasured" to -- measured --.
Line 60, please change "con" to -- on --.

Column 8,
Line 48, please change "ferroc,lanide" to -- ferrocyanide --.
Line 61, please change "approximated." to -- approximated --.
Line 66, please change "tile" to -- the --.

Column 9,
Line 36, please change "i," to -- is --.
Line 65, please change "ln$_2$ O$_3$" to -- In$_2$O$_3$ --.

Column 10,
Line 43, please change "working," to -- working -.
Line 59, please change "fonn" to -- form --.

Column 11,
Line 19, please change "what" to -- that --.
Line 32, please change "distamce" to -- distance --.
Line 50, please change "anda" to -- and a --.

Column 12,
Line 42, please change "fonn" to -- form --.
Line 53, please change "200 m" to -- 200 µm --.
Line 61, please change "counter/refercnce" to -- counter/reference --.

UNITED STATES PATENT AND TRADEMARK OFFICE
CERTIFICATE OF CORRECTION

PATENT NO. : 6,284,125 B1
DATED : September 4, 2001
INVENTOR(S) : Alastair McIndoe Hodges, Thomas William Beck and Oddvar Johansen It is certified that error appears in the above-identified patent and that said Letters Patent is hereby corrected as shown below:

Column 13,
Line 14, please change "formi" to -- form --.
Line 63, please change "prefornned" to -- preformed --.

Column 14,
Line 12, please change "fonn" to -- form --.
Line 26, please change "aci.ording" to -- according --.
Line 35, please change "arc" to -- are --.

Column 16,
Line 7, please change "flirther" to -- further --.

Signed and Sealed this

Nineteenth Day of August, 2003

JAMES E. ROGAN
*Director of the United States Patent and Trademark Office*